United States Patent [19]

Kletschka

[11] Patent Number: 5,055,005
[45] Date of Patent: Oct. 8, 1991

[54] FLUID PUMP WITH LEVITATED IMPELLER

[76] Inventor: Harold D. Kletschka, 1925 Noble Dr., Minneapolis, Minn. 55422

[21] Appl. No.: 593,695

[22] Filed: Oct. 5, 1990

[51] Int. Cl.$^5$ .............................................. F04B 17/00
[52] U.S. Cl. ................................... 417/356; 415/111; 415/900; 600/16; 604/151; 623/3
[58] Field of Search ............... 415/110, 111, 900, 112; 600/16, 17; 623/3; 417/356; 604/151

[56] References Cited

U.S. PATENT DOCUMENTS

| | | | |
|---|---|---|---|
| 845,816 | 3/1907 | Prindle | 415/112 |
| 888,654 | 5/1908 | Prindle | 415/102 |
| 1,026,101 | 5/1912 | Marsh | 415/111 |
| 2,864,552 | 12/1958 | Anderson | 415/112 |
| 3,122,101 | 2/1964 | Baker et al. | |
| 3,128,988 | 4/1964 | Mandroian | |
| 3,401,640 | 9/1968 | Fowler et al. | |
| 3,608,088 | 9/1971 | Dorman et al. | |
| 3,647,324 | 3/1972 | Rafferty et al. | 623/3 X |
| 4,135,253 | 1/1979 | Reich et al. | 415/112 X |
| 4,213,207 | 7/1980 | Wilson | 623/3 |
| 4,382,199 | 3/1983 | Isaacson | 623/3 X |
| 4,475,866 | 10/1984 | Kambe et al. | 415/112 |
| 4,589,822 | 5/1986 | Clausen et al. | 415/112 X |
| 4,688,998 | 8/1987 | Olsen et al. | 417/356 |
| 4,704,121 | 11/1987 | Moise | 623/3 |
| 4,844,707 | 7/1989 | Kletschka | 417/420 |

OTHER PUBLICATIONS

Brandt (May 1989) Levitation in Physics Science 243: 349–355.
Rafferty et al. (Mar. 1968) Artificial Heart I., Application of Nonpulsatile Force-Vortex Principle, Minnesota Med. 51: 11–16.
Rafferty et al. (Jun. 1968) Artificial Heart II., Application of Nonpulsatile Radially Increasing Pressure Gradient Pumping Principle, Minnesota Med. 51: 191:93.

Primary Examiner—Leonard E. Smith
Attorney, Agent, or Firm—Dorsey & Whitney

[57] ABSTRACT

A fluid pump with rotary impeller is disclosed which comprises an electromagnetically driven rotary impeller levitated by localized opposed fluid forces. Levitation by localized opposed fluid forces of an impeller driven by electromagnetic forces eliminates the need for bearings and seals in the driving mechanism. This avoids the heat build-up and leakage associated with other pumping mechanisms, which can be of importance for pumping of physiological fluids such as blood. The levitating fluid forces of the present invention are auto-adjusting, such that any attempted displacement of the impeller will automatically incur a corrective change in levitating fluid forces. However, fluid force sensors and regulators could be incorporated into the present invention if desired. The invention should be of use in numerous medical and non-medical applications where the benefits of impeller levitation by localized fluid forces are apparent.

19 Claims, 8 Drawing Sheets

FLUID PUMP WITH LEVITATED IMPELLER

BACKGROUND OF THE INVENTION

This invention relates to a fluid pump with rotary impeller, and more particularly, to a fluid pump including an electromagnetically driven rotary impeller levitated by localized opposed fluid forces. Levitation of the impeller by fluid forces allows for high efficiency in converting power into useful work. Thus, a relatively small energy source can be used and the life of the energy source is correspondingly extended. Moreover, use of a levitated impeller driven by electromagnetic forces eliminates the need for bearings and seals in the driving mechanism, thereby avoiding the heat build-up and leakage attendant with other rotary pump inventions. Such considerations can be of critical importance for pumping of physiological fluids such as blood.

A large number of mechanisms for pumping fluids have been described in the art, including, for example, peristaltic pumps, moving diaphragm pumps, piston-type pumps, and centrifugal or rotary pumps. Generally, a rotary pump includes a pumping chamber with inlet and outlet ports and an impeller mounted within the pumping chamber for rotation about an axis. Frequently the impeller is mounted on a shaft that extends through one or more seals and a bearing apparatus to a rotational driving mechanism outside the pumping chamber. Rotary pumps employing shaft-mounted impellers with shaft seals are exemplified in the following U.S. patents: Dorman et al. U.S. Pat. No. 3,608,088; Rafferty et al. U.S. Pat. No. 3,647,324; Reich et al. U.S. Pat. No. 4,135,253; Clausen et al. U.S. Pat. No. 4,589,822; Moise U.S. Pat. No. 4,704,121; Kletschka U.S. Pat. No. 4,844,707. Shaft seals are susceptible to wear and heat build-up, which can lead to leakage and, in the case of blood pumps, to thrombogenic (clot-forming) problems, denaturation of proteins, and embolic phenomena and the like.

Other pump inventions employ liquid or hydrostatic bearings to reduce heat build-up and/or to dissipate heat and to reduce frictional forces in rotation of the shaft and/or impeller. In these inventions liquid or gas is forced into narrow clearances between the shaft and various bearing assemblies or between the impeller and the impeller housing. The relatively thin fluid or gas films generated in these inventions are nevertheless subject to high shear forces and some incremental heat build-up. The following U.S. patents exemplify the use of such liquid or hydrostatic bearings: Prindle U.S. Pat. Nos. 845,816 and 888,654; Anderson U.S. Pat. No. 2,864,552; Baker et al. U.S. Pat. No. 3,122,101; Kambe et al. U.S. Pat. No. 4,475,866.

It would, therefor, be a significant advance in the art to provide a rotary fluid pump including a freely rotatable impeller immersed in the pumping fluid and suspended or levitated by localized fluid forces. This would eliminate the need for an impeller drive shaft with its attendant seals and bearings. A blood pump with magnetically suspended and rotated impeller is disclosed in Olsen et al. U.S. Pat. No. 4,688,998. While this invention eliminates the impeller drive shaft, bearings and seals, electrical power is required not only to drive the impeller but also to maintain the impeller in a suspended state. Moreover, the invention requires co-operating electromagnetic sets, sensors, suspension circuits, and sensing circuits for continuously adjusting the position of the impeller in the pump housing. It would therefore be a significant advancement in the art to provide a novel pump apparatus whereby the impeller is levitated and positioned in the pump fluid by an auto-adjusting mechanism and whereby it is possible for all input energy to be directed to rotation of the impeller. Such a novel pump apparatus is disclosed and claimed herein.

SUMMARY OF THE INVENTION

In accordance with the instant invention, a rotary pump is disclosed which is composed of a housing defining a pumping chamber with one or more pumping chamber inlet ports and a pumping chamber outlet port or ports; a rotatable impeller disposed in the pumping chamber for rotation about an axis; polarized electromagnetic means for rotating the impeller about the axis; and means for conducting fluid from a high pressure area at the periphery of the impeller and discharging the fluid in opposed directions within a lower pressure area in general proximity to the axis of the impeller, thereby levitating and stabilizing the impeller within the pumping chamber.

The impeller may be fashioned of various materials. In a preferred embodiment, the impeller may have a density similar to that of the fluid being pumped, thereby facilitating levitation and stabilization of the impeller within the pumped fluid.

The impeller may take various shapes, and may or may not possess vanes, depending upon the particular pump application. The impeller may be solid, or may possess internal fluid-filled space in communication with the pumping chamber or with the pumping chamber inlet and/or outlet ports. The impeller may possess a single inlet or opposed inlets near the axis of the impeller communicating with the pumping chamber inlet ports, and opposed outlets at the periphery of the impeller communicating with the pumping chamber outlet port or ports. The impeller may possess axially extending neck portions. Means for levitating the impeller may comprise conduits emanating from the vicinity of the pumping chamber outlet port and terminating in various configurations generally near the axially extending neck portion(s) of the impeller.

Polarized electromagnetic means for rotating the impeller may comprise conducting wire windings within the periphery of the pump housing electromagnetically coupled to permanent magnets housed within the periphery of the impeller. Alternatively, the polarized electromagnetic means for rotating the impeller may comprise conducting wire windings housed within a stator located internal to the impeller, the stator being in structural communication with the pump housing and electromagnetically coupled to one or more magnets housed within the internal structure of the impeller.

As used herein the term "fluid" means any aggregate of matter in which the molecules are able to flow past each other without limit and without the formation of fracture planes. The term includes gases, liquids, solutions, suspensions, slurries and gels and includes such specific substances as blood, plasma and serum.

DETAILED DESCRIPTION OF THE INVENTION

Figures 1, 2, 3:
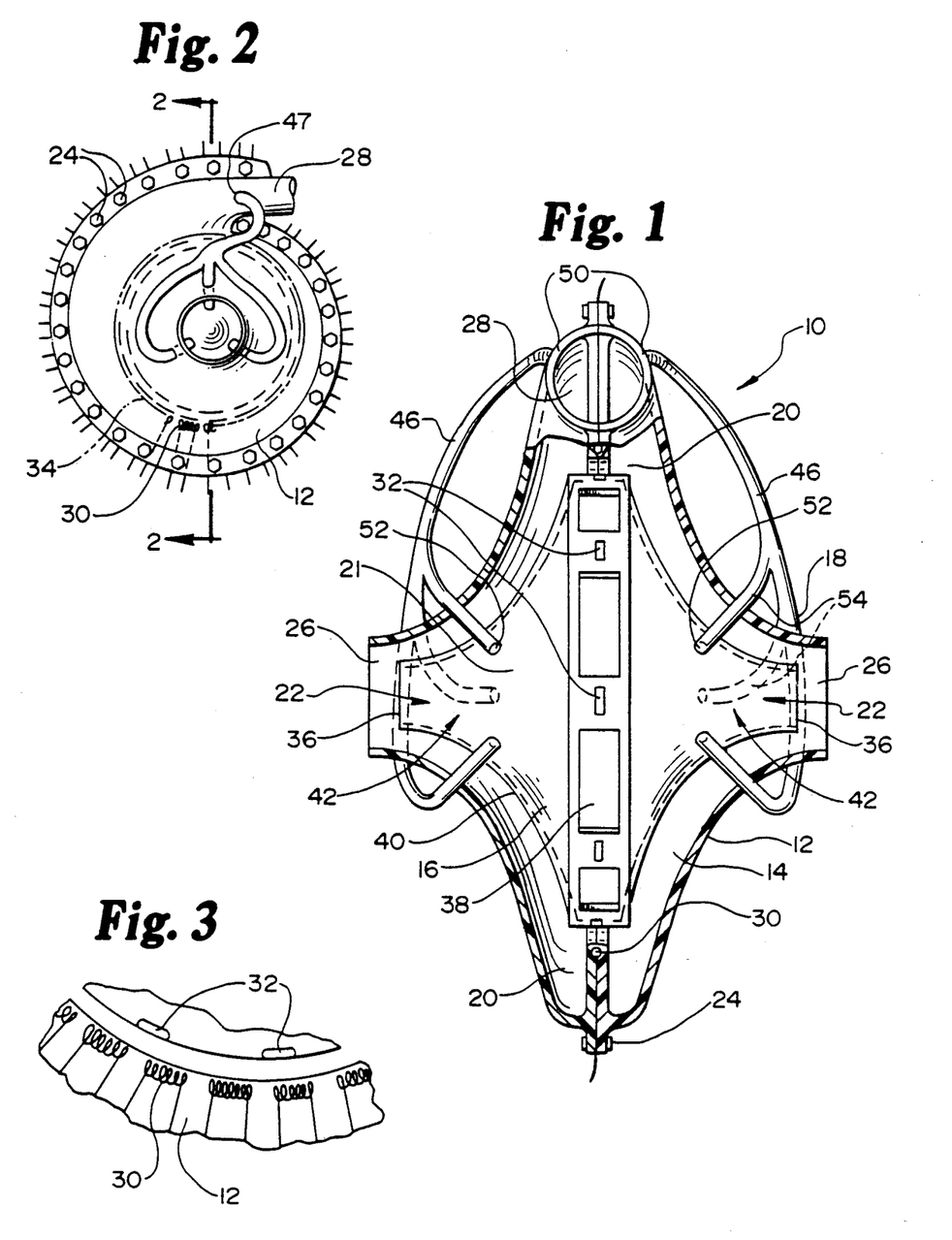
FIG. 1 is an axial sectional view of the preferred embodiment of the instant invention.
FIG. 2 is a side elevational view of the preferred embodiment shown in FIG. 1. The sectional view of FIG. 1 was taken along line 2—2 of FIG. 2.
FIG. 3 is a fragmentary sectional view of the impeller and pump housing, in an orientation analogous to that of FIG. 2.

FIG. 1 depicts the preferred embodiment of the pump 10 of this invention. The pump comprises a pump housing 12 defining a pumping chamber 14 through which fluid is pumped, an impeller 16, and means 18 for conducting fluid from a higher pressure region 20 near the periphery of the impeller, including pumping chamber outlet port 28, and discharging the fluid in a lower pressure region 21 in general proximity to the axis 22 of the impeller 16. The pump housing may be fashioned from two or more component parts secured together with fasteners 24 as shown in FIGS. 1 and 2. Alternatively, the pump housing may be fashioned from a single piece of material of seamless construction. The pump housing 12 also defines pumping chamber inlet ports 26 and a pumping chamber outlet port 28. The embodiment depicted in FIG. 1 possesses two pumping chamber inlet ports 26 and a single pumping chamber outlet port 28. The housing 12 could be configured, however, to define a single inlet port 26, as in FIG. 18, or more than two inlet ports, and/or multiple outlet ports. Other configurations of pumping chamber inlet and outlet ports for various applications of this invention will be apparent to those skilled in the art.

Figure 4:
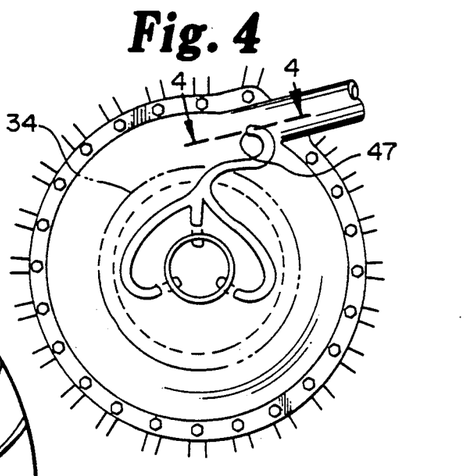
FIG. 4 is a side elevational view of a non-scrolled embodiment of the invention shown in FIG. 2.

The periphery of the pump housing 12 may incorporate electromagnetic wire windings 30 for rotating the impeller 16 about the impeller axis 22. One embodiment of the electromagnetic wire windings 30 is shown in FIG. 3, with windings spaced at regular intervals within the peripheral structure of the pump housing 12. In the embodiment shown in FIGS. 1, 2 and 3, the wire windings 30 are electromagnetically coupled to permanent magnets 32 housed within the peripheral structure of the impeller 16. The pumping chamber defined by the pump housing can be scrolled, as shown in FIG. 2, or non-scrolled, as shown in FIG. 4. However, the relative positions 34 of the electromagnetic windings 30 in relation to the impeller could be the same in either case, as shown in FIGS. 2 and 4.

Figure 19:
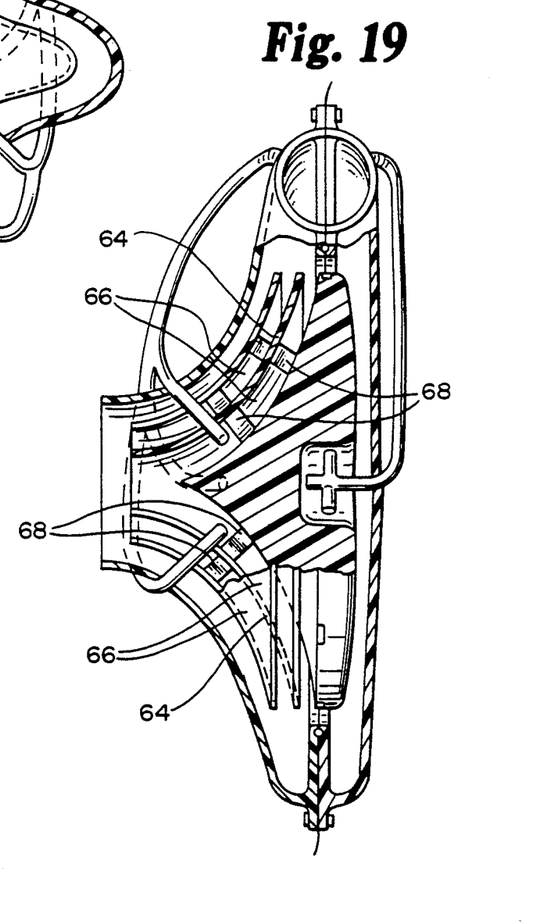
FIG. 19 is an axial sectional view of a further alternative embodiment of the present invention.
Figure 20:
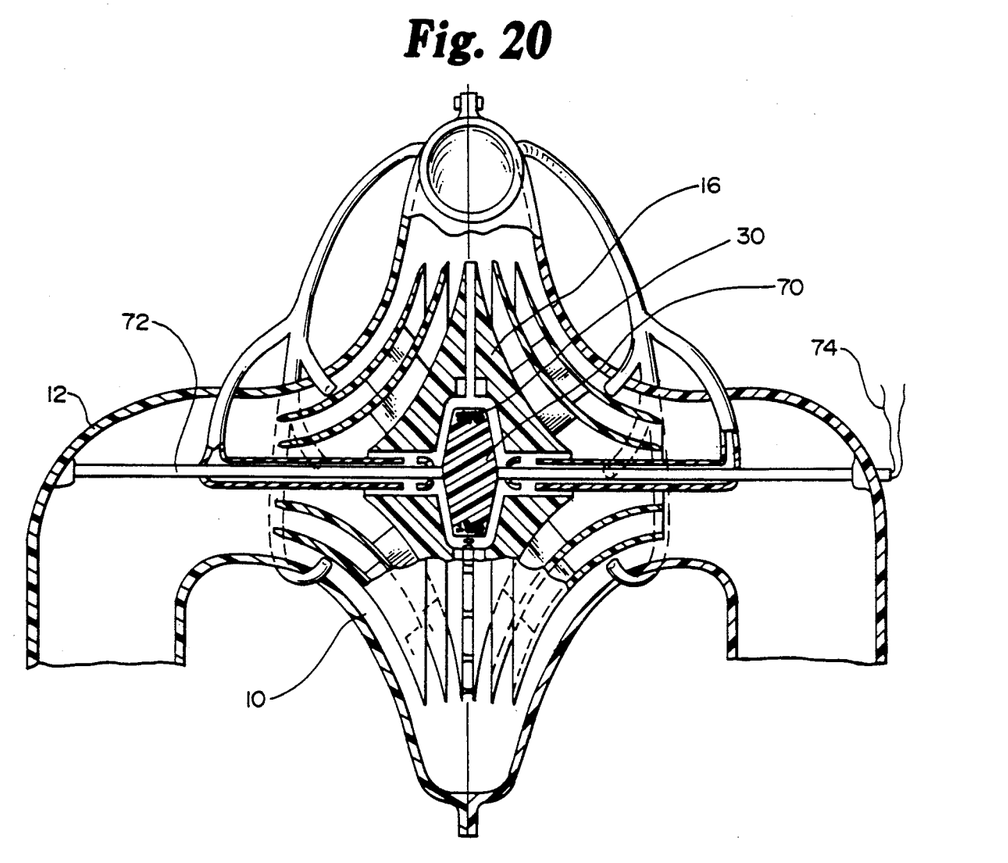
FIG. 20 is an axial sectional view of a final alternative embodiment of the present invention.

In an alternative embodiment as shown in FIG. 20, the wire windings 30 may be incorporated into a stator 70 located interior to the impeller 16, and about which the impeller 16 may rotate. The stator may be supported within the impeller by one or more supporting shafts 72 disposed along the axis of rotation of the impeller, the shafts 72 being in structural communication with the pump housing 12. The wire windings within the stator may be in electrical communication with one or more electrical power sources by means of wires 74 running from the stator 70 through the supporting shafts 72 to one or more of such electrical power sources located within or external to the fluid pump 10. Other configurations of electromagnetic means for rotating the impeller about an axis will be obvious to those skilled in the art. While FIG. 20 shows two inlet ports and one outlet port, one inlet port may be used as shown in FIG. 19, or the two inlet ports of FIG. 20 may be joined to form a single inlet port with a double, balanced inlet to the impeller. Multiple outlet ports may also be used.

Figure 18:
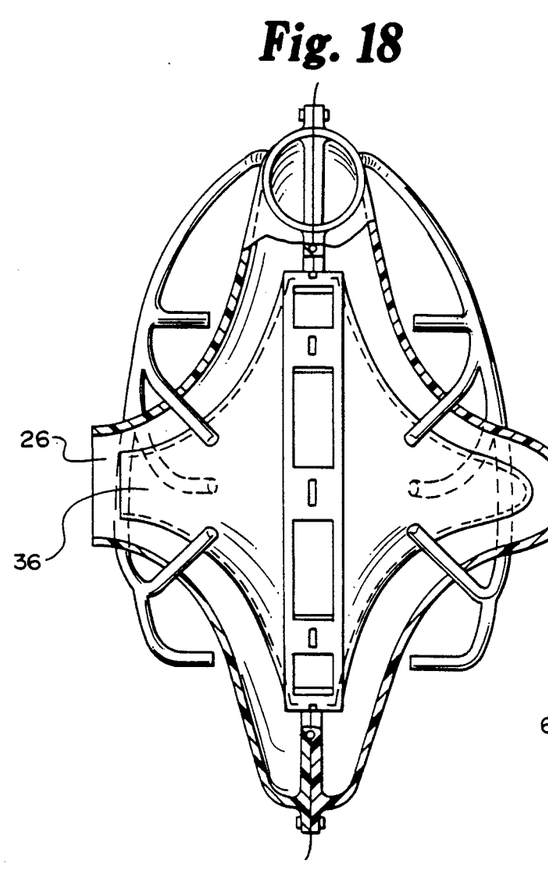
FIG. 18 is an axial sectional view of a further alternative embodiment of the present invention.

A preferred embodiment of the impeller 16 is shown in FIG. 1. In this embodiment, the impeller 16 possesses axially opposed inlets 36 communicating with the pumping chamber inlet ports 26, and opposed outlets 38 at the periphery of the impeller 16 communicating with the pumping chamber 14 and thereby with the pumping chamber outlet port 28. In operation, fluid enters the opposed inlets 36 of the impeller 16 from the pumping chamber inlet ports 26. An acceleration is imparted to the fluid due to frictional shear forces operating between the interior walls of the rotating impeller 16 and the fluid and between the molecules and particles of the fluid. Fluid exiting the impeller outlets 38 due to centrifugal forces operating within the accelerated fluid imparts circumferentially and radially directed fluid forces to the fluid within the pumping chamber 14. Similarly directed fluid forces are generated by frictional shear forces operating between the outer surfaces 40 of the impeller 16 and the fluid and between the molecules and particles of the fluid. In an alternative embodiment, the impeller posesses a single inlet 36, as in FIG. 18. However, principles of operation would be substantially the same as described above, whether the invention embodies a single housing inlet port, a single impeller inlet, or both, as shown in FIG. 18.

Figure 5:
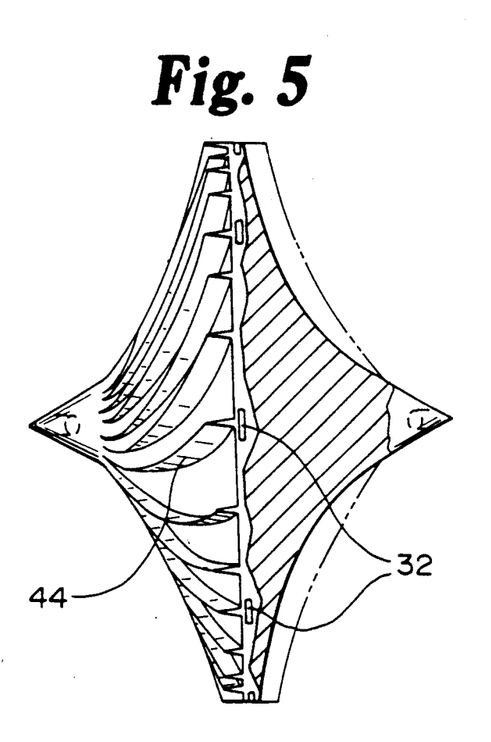
FIG. 5 is an end view of a solid impeller with exterior surface vanes.
Figure 6:
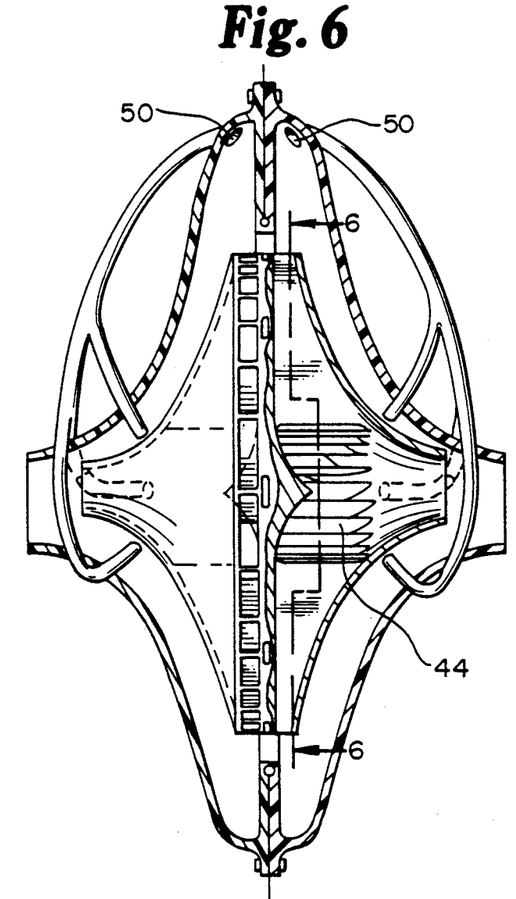
FIG. 6 is an axial sectional view of an alternative embodiment of the present invention.
Figure 7:
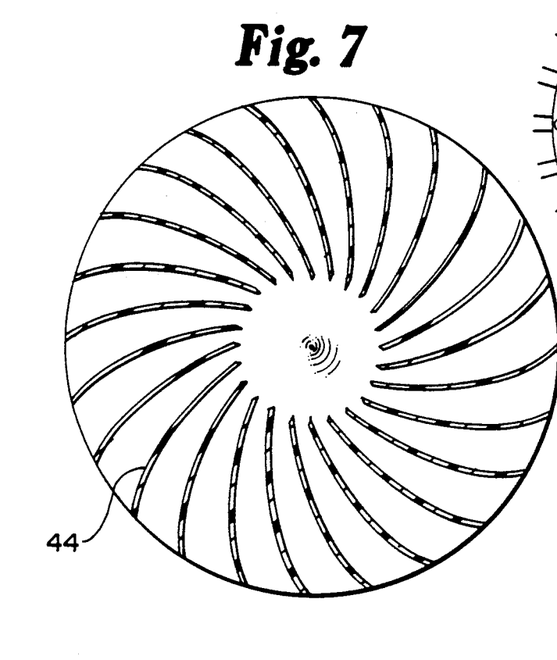
FIG. 7 is a sectional view of an impeller with internal vanes, taken along line 6—6 in FIG. 6.

In the preferred embodiment, the impeller includes opposed, axially extending neck portions 42 that encompass the opposed inlets, as shown in FIGS. 1,5, 6,8,9,10, and 14. Such neck portions could facilitate levitation of the impeller by providing appropriately directed surfaces upon which the levitating fluid forces may be directed. Numerous other configurations of the impeller 16, however, will be applicable to the concept embodied in the present invention—that of impeller levitation by localized fluid forces. For example, the total frictional force exerted by the impeller 16 on the fluid could be increased by providing additional partitions or walls within the impeller 16 transverse to the axis of rotation. Alternatively, partitions or walls 64 may serve to channel the fluid flow into separate compartments 66, connected by struts 68, extending from the region of an impeller inlet to the impeller outlets, as shown in FIGS. 19 and 20. FIG. 19 shows an embodiment of the invention with a single housing inlet port and a single impeller inlet. However, the compartmentalization shown in FIG. 19 could be readily adapted to the preferred embodiment of FIG. 1 or to an embodiment as shown in FIG. 20, with two housing inlet ports 26, two impeller inlets 36, and compartments 66 within both sides of the impeller 16. In a further embodiment, conveying channels could be incorporated into the impeller 16 to extend from an area in general proximity to the center of the interior of the impeller 16 to the impeller outlets 38. Such conveying channels are described in Rafferty et al., *Minnesota Medicine* 51: 191-193 (1968), incorporated herein in its entirety by reference thereto. As a further alternative embodiment, vanes 44 of various configurations could be placed on the outside of the impeller 16 as shown in FIG. 5, or on the inside of the impeller as shown in FIGS. 6,7,8, and 9.

Figure 10:
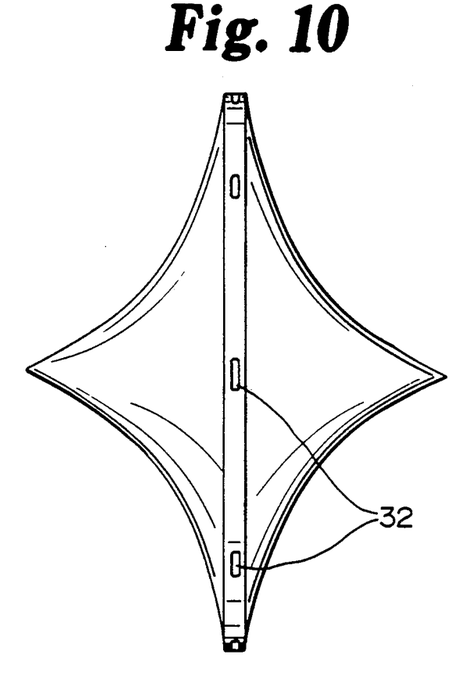
FIG. 10 is an end view of a solid impeller without exterior surface vanes.

Generally, in embodiments where the invention is used for the pumping of physiological fluids such as blood, vanes and other structures potentially capable of creating turbulence and/or excessive shear forces will be avoided. However, the invention is suitable for the pumping of any fluid (liquid or gas) where the advantages of impeller levitation by localized fluid forces are desired, and vanes and other structures designed to increase the shear forces generated by the impeller may be useful in such embodiments. In some embodiments, the fluid forces generated solely through interaction of the fluid with the rotating outer surface of the impeller may be adequate for the intended purposes(s). In such embodiments, the impeller 16 could be "solid," i.e., lacking an internal cavity in communication with the pumping chamber via impeller inlets and outlets. Such "solid" impeller embodiments are shown in FIGS. 5 and 10. "Solid" impellers of the present invention could include impellers with internal cavities for adjustment of impeller density, but such cavities would be sealed off from communication with the pumping chamber.

For biological or medical applications, it would be useful, but not necessary, for the impeller 16 to be of a density similar to that of the fluid being pumped. However in any application and regardless of the density of the impeller 16, it is only necessary that the levitating fluid forces be sufficient to counteract gravitational and inertial forces acting on the impeller 16. Biological and medical uses of the invention could include both human and veterinary applications. Similarly, the invention could be employed to function ex vivo (outside the body) or in vivo (inside the body), as well as in biological or non-biological and medical or non-medical uses not connected to a human or animal body.

Figure 11:
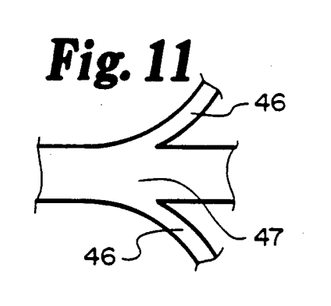
FIG. 11 is a simplified diagram of a conduit/outlet port junction, taken along line 4—4 in FIG. 4.
Figure 12:
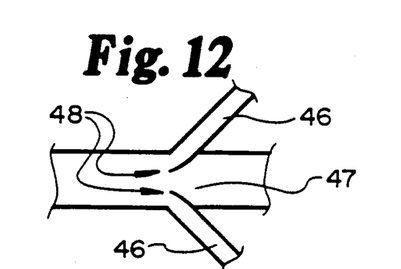
FIG. 12 is a simplified diagram of an alternative embodiment of a conduit/outlet port junction of the present invention.
Figure 13:
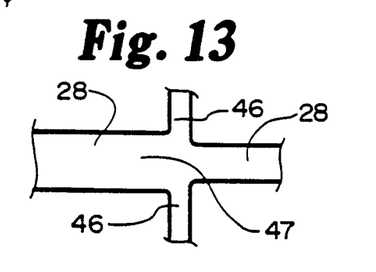
FIG. 13 is a simplified diagram of a further alternative embodiment of a conduit/outlet port junction of the present invention.

Referring again to the preferred embodiment shown in FIG. 1, means 18 for conducting fluid from a region of higher fluid pressure 20 near the periphery of the impeller 16 and discharging in a region of lower fluid pressure 21 so as to stabilize the impeller 16 by levitating fluid forces is comprised of conduits 46 emanating from the pumping chamber outlet port 28. The configuration of the conduit/outlet port junction must be such that the tendency for fluid within the conduit to move toward, rather than away from, the higher pressure fluid flow region within the outlet port 28, in accordance with the Bernoulli Law, is overcome. Referring to FIG. 1, the side-elevational views of the invention 10 as shown in FIGS. 2 and 4, and the fragmentary view of the conduit/outlet port junction 47 shown in FIG. 11, the conduit 46 may leave the outlet port 28 at an orientation tangential to the direction of fluid flow within the outlet port in order to achieve the desired result. Alternatively, as shown in FIG. 12, deflectors 48 may be placed within the junction to facilitate diversion of fluid flow into the conduits 46. In a further embodiment as shown in FIG. 13, the diameter of the outlet port "downstream" from the junction 47 may be made smaller than the diameter of the outlet port "upstream" from the junction 47. As shown in FIG. 13, depending on the relative proportions of the diameters of the outlet port 28 on either side of the junction 47, the conduits 46 could emanate from the outlet port 28 perpendicular (FIG. 13), or even retrograde, to the direction of fluid flow in the outlet port 28. Other configurations of the conduit/outlet port junction for overcoming adverse fluid flow dynamics due to the Bernoulli Law will be apparent to those skilled in the art. Configurations analogous to those described above may be used within any fluid flow region of the invention wherein the principles of the Bernoulli Law create undesired fluid flow dynamics.

Figure 8:
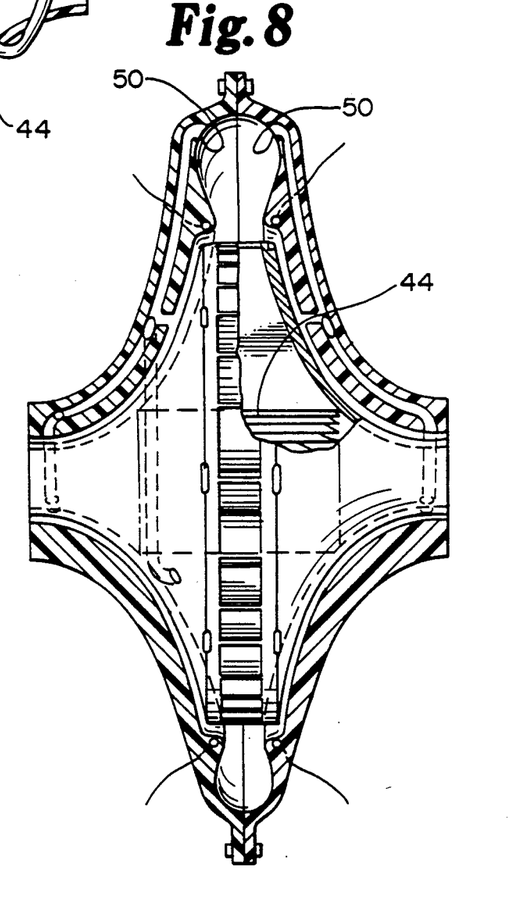
FIG. 8 is an axial sectional view of an alternative embodiment of the present invention.

The conduits 46 may emanate from separate sites 50 on the outlet port 28, as shown in FIG. 1 or from a common tap-off point in the region of the outlet port. In alternative embodiments, as shown in FIGS. 6, 8, 9 and 14, the conduits may emanate from a separate site or sites off of any region of the pump housing 12 that is in usable proximity to a region of higher fluid pressure. In further alternative embodiments, fluid pressure in the conduits 46 may be developed from a separate source, such as a graft from an artery to the conduit or from a separate pump or pressure source. The conduits may travel in a region exterior to the pump housing, as shown in FIGS. 1, 6, 8 and 14. Alternatively, the conduits may travel within or inside the walls of the pump housing, as shown in FIG. 8.

Referring again to the preferred embodiment shown in FIG. 1, each conduit 46 terminates in structure defining three fluid jet ports 52 within a lower fluid pressure region in the pumping chamber inlet port 26 in general proximity to the axially extending neck portion 42 of the impeller 16. The fluid jets emanating from three fluid jet ports 52 on both sides of the impeller 16, as shown in FIG. 1, define a fluid plane or circle of orientation suitable to prevent the impeller 16 from moving in the axial or radial directions so as to touch the walls of the pump housing 12 or distal ends of the fluid jet ports 52. Each conduit 46 could terminate in more than three fluid jet ports, depending on the shape of the impeller and fluid flow dynamics in specific alternative embodiments of the invention.

In the configurations described above, and in alternative embodiments described below, the fluid jet ports are oriented such that the levitating fluid forces are auto-adjusting. That is, a change in corrective force will be automatically or inherently incurred by any attempted displacement in location of the impeller. Alternatively, sensors and fluid flow regulating devices could be incorporated into the conduits 46 and/or fluid jet ports 52 to adjust or assist in adjusting for any attempted displacement in location of the impeller 16. The fluid jet ports 52 may protrude into the pumping chamber 14, as shown in FIG. 1, or may be flush with the inner wall of the housing 12 as shown in FIG. 8. Alternatively, a combination of protruding and nonprotruding (flush) fluid jet ports may be employed.

Figures 9, 15, 16, 17:
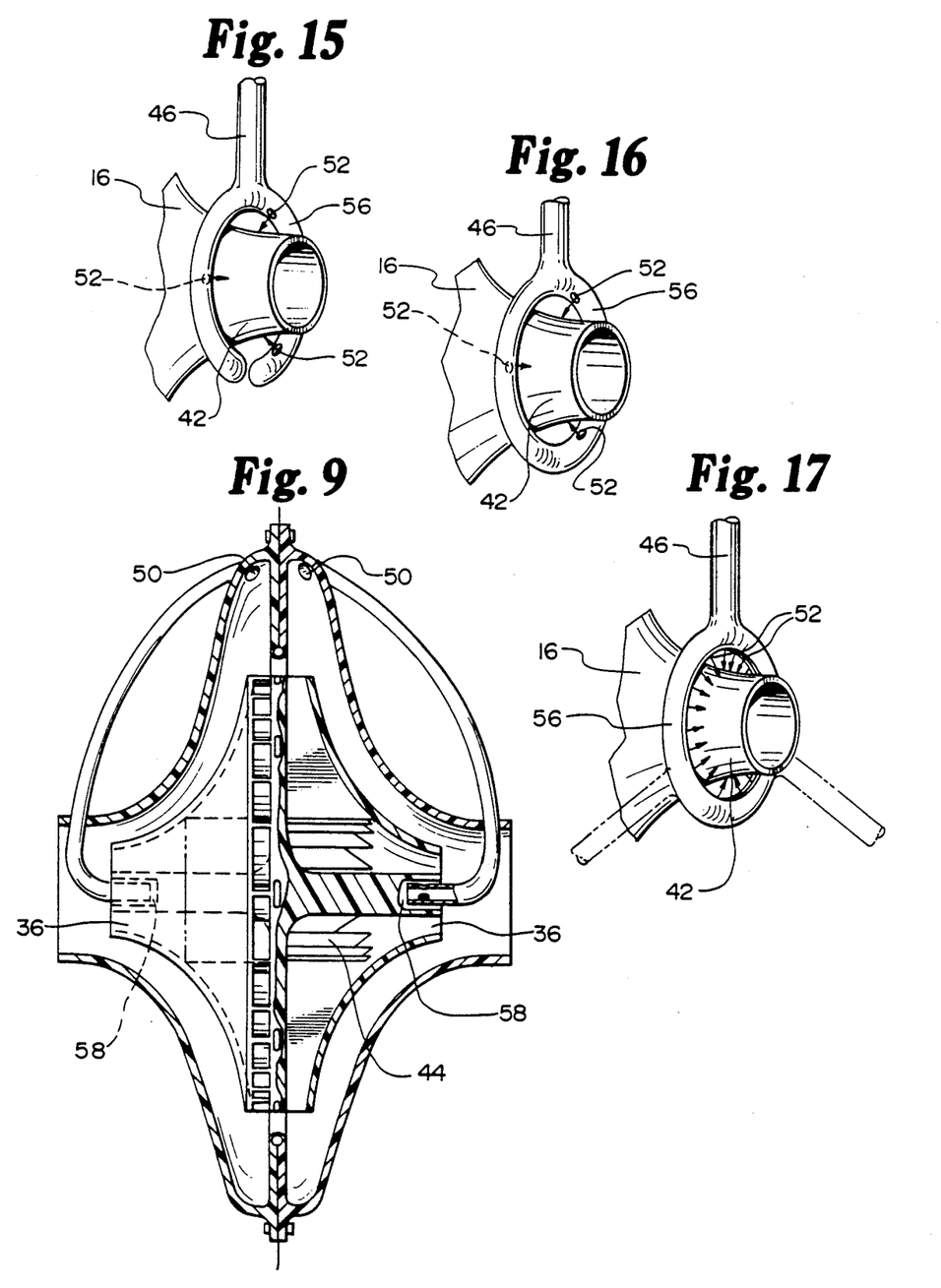
FIG. 9 is an axial sectional view of an alternative embodiment of the present invention.
FIG. 15 is a fragmentary perspective view of the axially extending neck portion of an impeller with associated distal end of a conduit.
FIG. 16 is a fragmentary perspective view of the axially extending neck portion of an impeller with an alternative embodiment of the distal end of a conduit.
FIG. 17 is a fragmentary perspective view of the axially extending neck portion of an impeller with a further alternative embodiment of the distal end of a conduit.

The fluid jet ports 52 may be associated with distinct branches 54 of each conduit 46, as shown in FIG. 1. Alternatively, the fluid jet ports 52 may be incorporated into the distal end of a conduit 46 that has been configured to partially (FIG. 15) or completely (FIGS. 16, 17) encompass the axially extending neck portion 42 of the impeller 16. The fluid jet ports 52 may be formed from distinct openings within the distal structure 56 of the conduit 46, as shown in FIGS. 15 and 16. Alternatively, the entire inner surface of the conduit distal structure could be configured to form a single continuous and circumferential jet port 52 of the appropriate size, location, and orientation, as shown in FIG. 17.

Figure 14:
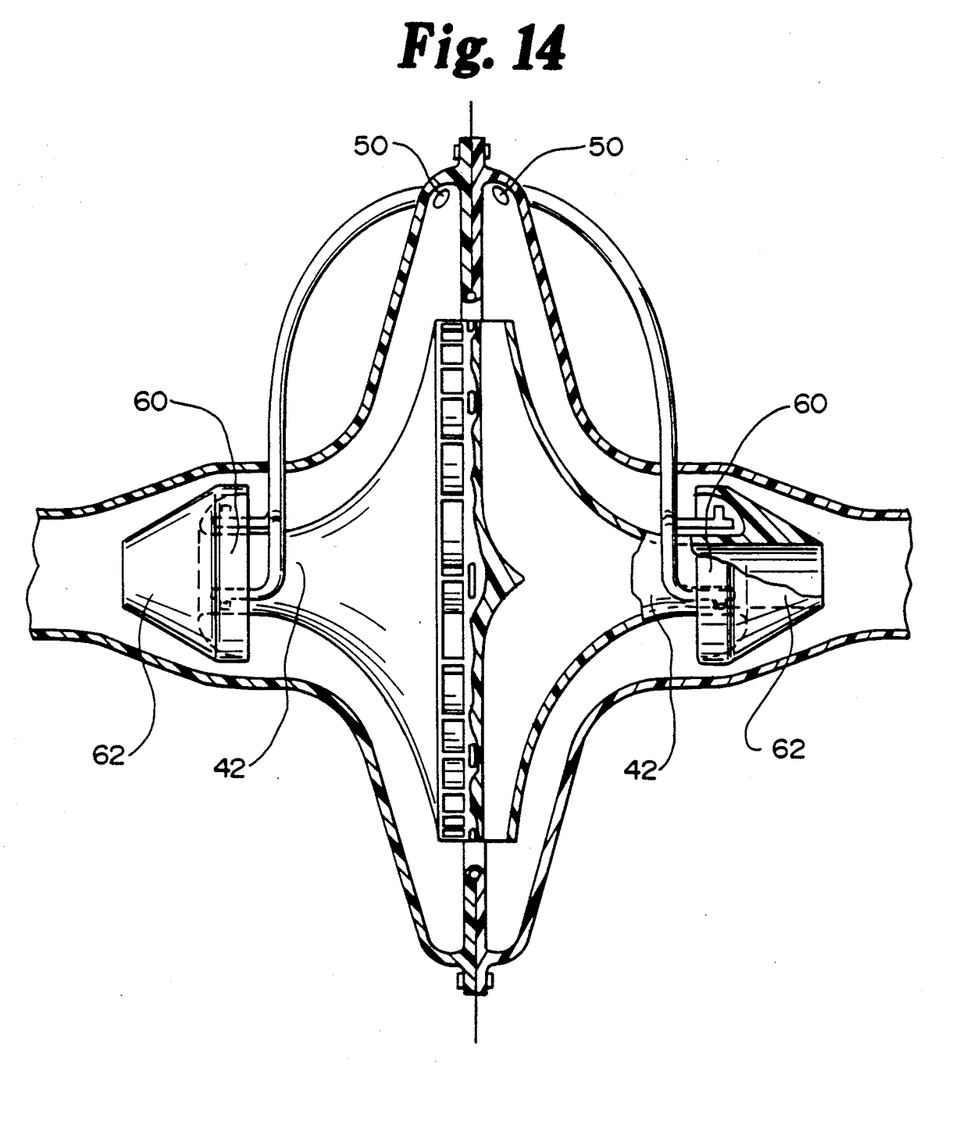
FIG. 14 is an axial sectional view of an alternative embodiment of the present invention.

The structure of the impeller 16 may be modified to accommodate additional alternative configurations of the conduits and associated fluid jet ports. For example, levitating fluid jets may be discharged within structure 58 incorporated into the impeller inlets 36, as shown in FIGS. 9 and 20. In an alternative embodiment to that shown in FIG. 9, structure 58 may be configured to extend completely through the interior of the impeller, thereby forming an axial cavity extending from the left impeller inlet to the right impeller inlet. The left and right conduits then may be made continuous through such cavity, with the fluid jet ports positioned along the conduits within the cavity to provide appropriate levitating fluid forces within the cavity. Alternatively, the levitating fluid jets may be discharged into the concave surface area 60 of a frusto-conical hood element 62 forming part of the distal structure of the axially extending neck portion 42 of the impeller 16, as shown in FIG. 14. Various additional configurations of conduits and fluid jet ports for levitating and stabilizing an impeller of the present invention will be obvious to those skilled in the art.

Various methods may be employed to start the pumping mechanism of the present invention. The pump housing and its inlet and outlet ports, the impeller and its inlets and outlets, the conduits and fluid jet ports, and the vessels or other passageways leading to and from the pump housing may be primed with fluid prior to activation of the electromagnetic means for rotating the impeller. Fluid may be introduced into the invention at various locations from external sources. If necessary, an external pressurizing mechanism may be used to introduce an appropriate priming fluid and to expel air potentially trapped within the spaces of the invention. Once the invention has been primed, activation of the electromagnetic means may be sufficient to overcome the inertia of the impeller and to initiate rotation of the impeller. This would lead nearly immediately to generation of levitating fluid forces emanating from the fluid jet ports. As the speed of rotation of the impeller reached operating levels, the levitating fluid forces generated would bring the impeller to its operating position within the pump housing.

With an impeller of a density the same as, or similar to, that of the fluid, levitating fluid forces will bring the impeller to its operating position very shortly after the activated electromagnetic means has induced the first several rotations of the impeller. In any case, most embodiments of the invention incorporate structural constraints on displacement of the impeller from its operating position within the housing. For example, the spacing between the conduit jet port structure and the impeller, as shown in FIGS. 1, 6, 8, 9, and 14, should be less than the spacing between the impeller and that portion of the housing encompassing the electromagnetic wire windings. Other structural constraints on displacement of the impeller are shown in FIGS. 15, 16, and 17. Alternatively, an arrester or other form of arresting bearing surface, distinct from the structure comprising the fluid jet ports, extending circumferentially around the axially extending neck portion of the impeller, may be located within the pump housing. Again, the distance between the arresting bearing surface and the impeller should be less than the distance between the impeller and that portion of the housing encompassing the electromagnetic wire windings. Such structural constraints as described above, as well as others known to those skilled in the art, would facilitate starting of the pumping mechanism, since the impeller magnets would not be in a "freeze-up" contact with the electromagnetic wire windings at start-up, and movement of the impeller from its start-up position to its operating position would entail only a slight positional reorientation.

In addition, in certain applications, such as pumping human or animal blood, the surfaces of the impeller, the structure comprising the fluid jet ports, and, if present, the arresting surfaces, should preferably be manufactured of smooth materials having low coefficients of friction. The combination of only minimal required spatial reorientation of the impeller at the start-up phase, with low coefficient of friction between the impeller and structural constraints, would facilitate initial rotation of the impeller with rapid reorientation to the operating position. This will be so even with an impeller of density dissimilar to that of the fluid being pumped.

If the density of the impeller were such that even the above configurations and surface characteristics were insufficient to allow start-up of the primed invention, other embodiments could be constructed to overcome this problem. For example, the structure of the impeller inlet(s) may incorporate one or more shafts extending axially from the impeller into the pumping chamber or into the pumping chamber inlet ports. An external drive mechanism coupled to the shaft could provide the necessary force to allow initial rotation of the impeller, until the generated levitating fluid forces allowed for maintenance of impeller rotation by the electromagnetic means. At this point, the external drive mechanism could be disconnected or disengaged.

The preferred application of pumps of the instant invention is in the medical field for the pumping of blood, although the invention as embodying impeller levitation by localized fluid forces will be useful in numerous other medical and non-medical pumping applications. In human medicine, it is unknown whether or not a pulsatile blood flow is required for optimum short-term or long-term clinical efficacy of artificial blood pumps. The rotary impeller 16 of the present invention is most conveniently operated in a continuous, non-pulsatile mode. However, depending on the configuration and mode of operation of the electromagnetic means for driving the impeller 16, the mode of operation may be pulsatile, or even intermittent. Likewise, the levitating fluid jets could be operated in a continuous, pulsatile, or intermittent mode. Alternatively, the operation of the impeller and levitating fluid jets could fluctuate between continuous, pulsatile, and intermittent modes, or between any combination of these modes, depending on the structure and intended use of specific embodiments of the present invention. Appropriate modes of operation, including valving or other means of changing the cross-sectional area of fluid flow in the pumping chamber inlet and outlet ports and in the levitating conduits, will be obvious to those skilled in the art.

From the foregoing, it will be obvious to those skilled in the art that various modifications in the above described devices can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for stabilizing the position of a rotatable impeller suspended in fluid in a pumping chamber, the impeller having an axis of rotation, the pumping chamber having a pumping chamber inlet port and a pumping chamber outlet port, which comprises: the step of conducting fluid from the periphery of the impeller and discharging the fluid in the pumping chamber in general proximity to the axis of the impeller in opposed directions to thereby stabilize the position of the impeller in the pumping chamber by levitating fluid forces.

2. The method of claim 1, wherein the impeller possesses opposed inlets in proximity to the axis of rotation and opposed outlets at the periphery of the impeller spaced from the inlets communicating with the pumping chamber outlet port.

3. The method of claim 1 wherein the impeller possesses a single inlet in general proximity to the axis of the impeller communicating with the pumping chamber inlet port, and opposed outlets at the periphery of the impeller spaced from the inlets communicating with the pumping chamber outlet port.

4. The method of claim 1 and means for regulating the discharge of the fluid toward the impeller.

5. A fluid pump comprising:
   a. a housing defining a pumping chamber, a pumping chamber inlet port and a pumping chamber outlet port,
   b. a rotatable impeller, disposed in the pumping chamber for rotation about an axis,
   c. polarized electromagnetic means for rotating the impeller about the axis, and
   d. means for conducting fluid from the peripheral region of the impeller and discharging the fluid in opposed directions in general proximity to the axis of the impeller, to thereby stabilize the impeller by levitating fluid forces.

6. The fluid pump of claim 5, wherein the impeller possesses a single inlet in proximity to the axis of the impeller communicating with the pumping chamber inlet port, and opposed outlets at the periphery of the impeller spaced from the inlets communicating with the pumping chamber outlet port.

7. The fluid pump of claim 5 wherein said electromagnetic means comprise conducting wire windings housed within the peripheral structure of the pump housing electromagnetically coupled to one or more magnets housed within the peripheral structure of the impeller.

8. The fluid pump of claim 5 wherein said electromagnetic means comprise conducting wire windings housed within a stator located internal to the impeller, said stator being in structural communication with the pump housing, and wherein said windings are electromagnetically coupled to one or more magnets housed within the internal structure of the impeller.

9. The fluid pump of claim 5, wherein the density of said impeller is similar to that of the fluid.

10. The fluid pump of claim 9, wherein the impeller possesses opposed inlets in proximity to the axis of the impeller communicating with the pumping chamber inlet port, and opposed fluid outlets at the periphery of the impeller spaced form the fluid inlets communicating with the pumping chamber outlet port.

11. The fluid pump of claim 10, wherein said impeller includes opposed axially extending neck portions, the proximal portion of each said neck portion being attached to, and centered on, a central axial surface of the impeller, and the distal end of each said neck portion being housed within the corresponding adjacent pumping chamber inlet port.

12. The fluid pump of claim 11 wherein said means for conducting fluid from the periphery of the impeller and discharging so as to stabilize the impeller by levitating fluid forces is comprised of conduits emanating from the pumping chamber outlet port, each said conduit terminating in structure defining three or more fluid jet ports within the pumping chamber inlet port in general proximity to the axially extending neck portion of the impeller.

13. The fluid pump of claim 12 wherein said impeller includes a frusto-conical hood element attached to the distal end of each axially extending neck portion, said hood element having a medially-facing concave surface and a distally-facing convex surface.

14. The fluid pump of claim 13 wherein the fluid jet ports of each conduit terminate within a region of the pumping chamber inlet port subtended by the concave surface of the frusto-conical hood element.

15. The fluid pump of claim 5, wherein the impeller possesses opposed inlets in general proximity to the axis of the impeller, communicating with the pumping chamber inlet port, and opposed outlets at the periphery of the impeller spaced from the inlets, communicating with the pumping chamber outlet port.

16. The fluid pump of claim 15, wherein said impeller includes opposed axially extending neck portions, the proximal portion of each said neck portion being attached to, and centered on, a central axial surface of the impeller, and the distal end of each said neck portion being housed within the corresponding adjacent pumping chamber inlet port.

17. The fluid pump of claim 16 wherein said means for conducting fluid from the periphery of the impeller and discharging so as to stabilize the impeller by levitating fluid forces is comprised of conduits emanating from the pumping chamber outlet port, each said conduit terminating in structure defining three or more fluid jet ports within the pumping chamber inlet port in general proximity to the axially extending neck portion of the impeller.

18. The fluid pump of claim 17 wherein said impeller includes a frusto-conical hood element attached to the distal end of each axially extending neck portion, said hood element having a medially-facing concave surface and a distally-facing convex surface.

19. The fluid pump of claim 18 wherein the fluid jet ports of each conduit terminate within a region of the pumping chamber inlet port subtended by the concave surface of the frusto-conical hood element.

* * * * *